United States Patent [19]

Hayes et al.

[11] Patent Number: 5,263,490
[45] Date of Patent: Nov. 23, 1993

[54] MUSCLE FUNCTION ASSESSMENT

[75] Inventors: James P. Hayes, Pickerington; James L. Tiefenthal, Columbus; Mark A. McCamish; Jeffrey R. Ross, both of Worthington, Ohio

[73] Assignee: Abbott Laboratories, Abbott Park, Ill.

[21] Appl. No.: 920,080

[22] Filed: Jul. 27, 1992

[51] Int. Cl.$^5$ .............................................. A61B 5/05
[52] U.S. Cl. .................................. 128/741; 128/782; 73/379; 364/413.02
[58] Field of Search ................ 128/741, 739, 740, 742, 128/744, 745, 746, 733, 774, 782, 783, 421, 419 R; 73/379; 364/413.01, 413.02

[56] References Cited

U.S. PATENT DOCUMENTS

| | | | |
|---|---|---|---|
| 3,830,226 | 8/1974 | Staub et al. | 128/741 |
| 3,898,983 | 8/1975 | Elam | 128/741 |
| 4,064,870 | 12/1977 | Dumitrescu et al. | 128/741 |
| 4,236,528 | 12/1980 | Stanec et al. | 128/741 |
| 4,387,723 | 6/1983 | Atlee, III et al. | 128/734 |
| 4,811,742 | 3/1989 | Hassel et al. | 128/733 |
| 4,896,289 | 1/1990 | Svinicki et al. | 364/900 |
| 4,962,766 | 10/1990 | Herzon | 128/741 |
| 5,125,406 | 6/1992 | Goldstone et al. | 128/642 |
| 5,131,401 | 7/1992 | Westenskow et al. | 128/741 |

OTHER PUBLICATIONS

"Voluntary Strength and Fatigue", Merton, Journal of Physiology, 123:553-564 (1954).
"Human skeletal muscle function:description of tests and normal values", Edwards et al., Clinical Science and Molecular Medicine, 52:283-290 (1977).
"Relaxation rate of constituent muscle-fibre types in human quadriceps", Wiles et al., Clinical Science, 56: 47-52 (1979).
"Contractile properties and fatigue of the diaghram in man", Moxham et al., THORAX, 36:164-168 (1981).
"Skeletal muscle function in malnutrition", Lopes et al., American Journal of Clinical Nutrition, 36:602-609 (1982).
"Skeletal muscle function during hypocaloric diets and fasting: a comparison with standard nutritional assesment parameters", Russell et al., American Journal of Clinical Nutrition, 37:133-138 (1983).
"The effect of fasting and hypocaloric diets on the functional and metabolic characteristics of rat gastrocnemius muscle", Russell et al., Clinical Science, 67: 185-194 (1984).
"Muscle function testing in the hospitalized patient: Implications for starvation an refeeding", Greig et al., IEEE Engineering In Medicine and Biology Magazine, Jun. 1986:pp. 36-39.
"Bulk or Bounce-The Object of Nutritional Support", Jeejeebhoy et al., Journal of Parenteral and Enternal Nutrition, vol. 12 No. 6, pp. 539-549 (1988).
"Skeletal muscle relaxation rate after fasting or hypocaloric feeding", Nishio et al., Journal of Applied Physiology, 71(1):204-209 (1991).

*Primary Examiner*—Stephen C. Pellegrino
*Assistant Examiner*—Guy V. Tucker
*Attorney, Agent, or Firm*—Lonnie R. Drayer; Donald O. Nickey

[57] ABSTRACT

An apparatus may be employed for determining the relaxation rate of a muscle which has been caused to contract in response to an electrical stimulus. The relaxation rate may be used in evaluating a person's nutritional status. The apparatus has support for supporting the forearm and wrist of a person in a palm-up position with the wrist extended. An electrical stimulus is applied to the person's ulnar nerve, and the force exerted upon a load cell by the person's thumb is measured. A computer is employed for receiving, storing, plotting and analyzing the force data collected by a transducer.

7 Claims, 16 Drawing Sheets

```
<↕▲>-Move Cursor   <PgUp/Dn>-View More Files   Enter-Select   Esc-Exit   F1-Help

SUBJECT1 06/26/92 20:08   SUBJECT2 06/13/92 18:07   SUBJECT3 07/07/92 21:14
```

---

Muscle Force Assessment System v2.0 r1.42            Selected File: SUBJECT1

FIG-6

Subject  Parameters  Grip  Locate  Space-Execute  Esc-Exit  F1-Help

```
———— Subject ————        —— Grip ——        Parameters..:♦1/1   2/1   3/1
Name:-----------------                     Lead In....:   1.1   2.1   3.1  Sec
     000lbs, 0ft 00in, 00yrs   1)  30.6    Lead Out...:   ■     ■     ■    Sec
Hand:R,R (Dominant, Tested)    2)  38.5    S-Duration.:   1.0   1.0   1.0  Sec
Test:00/00/92 Study:00/00/92   3)  35.9    S-Intensity:01.0  01.0  01.0   mA
                               4)  27.3    S-Frequency:010   010   010    cps
                               5)  28.0    S-Width....:010   010   010    uSc
Filename:_____.MFA/PTS                  Force Peak.:  16    18    21   N
                                           Force Peak.: 100   113   131   %
Comments:-----------------                 Relax Rate.:  -9    -5    -3   %
         -----------------
```

FIG-7

MUSCLE FUNCTION ASSESSMENT

FIELD OF THE INVENTION

The present invention relates generally to the assessment of a person's nutritional status and more specifically to an apparatus and method for assessing a person's nutritional status.

BACKGROUND OF THE INVENTION

It is very simple to identify the severely malnourished patient by current body composition analysis techniques. However, identification of early malnutrition is difficult. The study of muscle function as an indicator of malnutrition was chosen due to the obvious effects of muscle wasting seen during prolonged malnutrition. In patients with malnutrition, changes in muscle contractility, relaxation rate and endurance (muscle function) may precede the detectable changes in body composition. The available evidence suggests that malnutrition may alter muscle function by altering the ability of the muscle to regulate the calcium content of the muscle fiber.

Moxhan has demonstrated the similarity of muscle function between various groups of muscles including the sternocleidomastoid, quadriceps, adductor pollicis and diaphragm. This similarity was seen when results were normalized by the maximal force obtained from each group. "Contractile properties and fatigue of the diaphragm in man", Moxham et al., *THORAX* 36:164-168 (1981). Therefore it can be postulated that the adductor pollicis muscle function represents muscle function as a whole. Function of the adductor pollicis muscle can be assessed by electrical stimulation of the ulnar nerve. It has been shown by various investigators that the maximal relaxation rate in malnourished individuals differs significantly from normal controls.

The present invention provides an apparatus and method which may be employed for assessing muscle function as an indication of the nutritional status of a person.

DISCUSSION OF THE PRIOR ART

A device for the stimulation of the adductor pollicis muscle is described in "Voluntary strength and fatigue", Merton, *JOURNAL OF PHYSIOLOGY*, 123:553-564 (1954). A modification of this device is described in "Human skeletal muscle function: description of tests and normal values", Edwards et al., *CLINICAL SCIENCE AND MOLECULAR MEDICINE*, 52:283-290 (1977). Muscle function testing using the adductor pollicis in malnourished patients is described in "Skeletal muscle function in malnutrition", Lopes et al., *AMERICAN JOURNAL OF CLINICAL NUTRITION*, 36:602-609 (1982). The effects of hypocaloric diets and fasting on skeletal muscle function have been described in: "The effect of fasting and hypocaloric diets on the functional and metabolic characteristics of rat gastrochemius muscle", Russell, et al., *CLINICAL SCIENCE*, 67: 185-194 (1984); "Skeletal muscle function during hypocaloric diets and fasting: a comparison with standard nutritional assessment parameters", Russell et al., *AMERICAN JOURNAL OF CLINICAL NUTRITION*, 37:133-138 (1983); and "Skeletal muscle relaxation rate after fasting or hypocaloric feeding", Nishio et al., *JOURNAL OF APPLIED PHYSIOLOGY*, 71(1):204-209 (1991). However; the prior art does not contain an easily employed apparatus for performing a muscle force assessment procedure conveniently in a clinical setting. Such an apparatus is provided by the present invention.

BRIEF DESCRIPTION OF THE DRAWINGS

The features of the invention which are believed to be novel are set forth with particularity in the appended claims. The present invention, both as to its structure and manner of operation, may best be understood by reference to the following detailed description, taken in accordance with the accompanying drawings in which:

FIGS. 6-12 are pictorial representations of what may appear on a computer screen during the muscle force assessment procedure;

DETAILED DESCRIPTION OF THE INVENTION

An apparatus for assessing muscle function, as an indicator of nutritional status, includes a base plate assembly for maintaining a person's arm and hand in a preferred position, a means for applying an electrical stimulus to a muscle, and a means for measuring the muscle's reaction to the stimulus.

Figure 1:
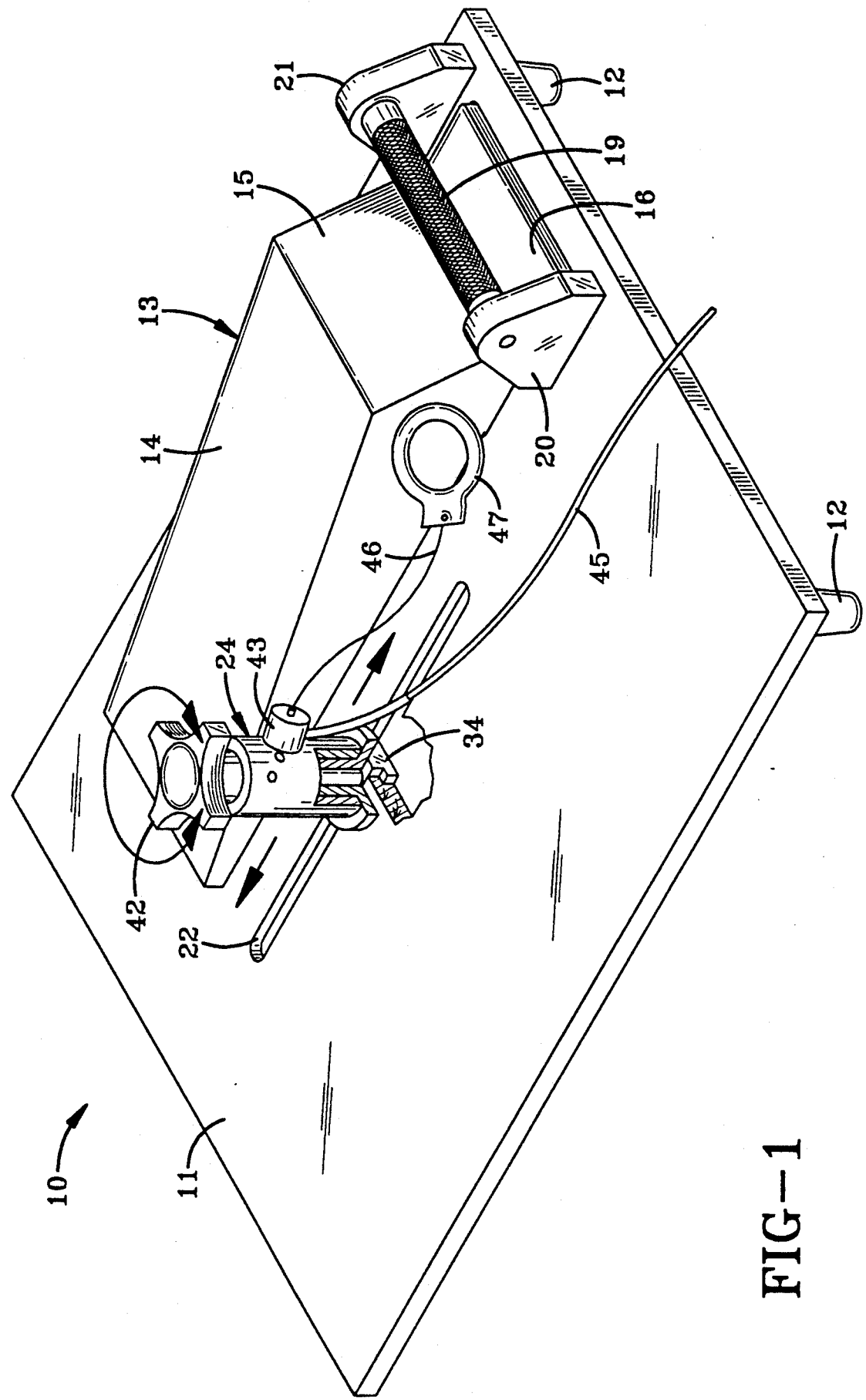
FIG. 1 is a perspective view of partially broken away, a baseplate assembly which is to a first embodiment of the present invention.
Figure 2:
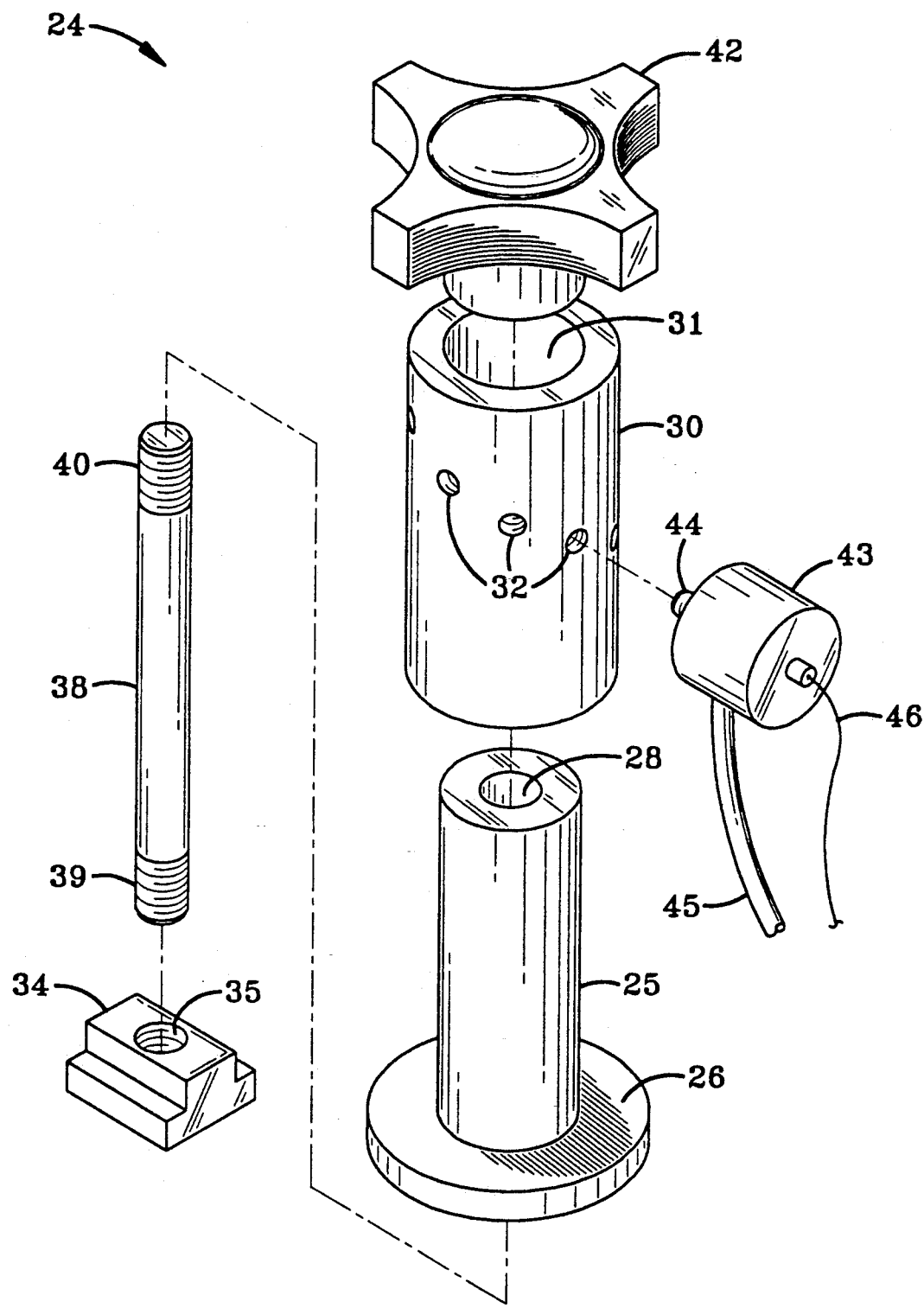
FIG. 2 is an exploded view of an anchor assembly which is a component of the muscle function assessment device shown in FIG. 1.

Referring first to FIGS. 1 and 2 there are shown a base plate assembly (partially broken away) and an enlarged view of an anchor assembly 24 which is a component of the base plate assembly. In describing the invention the dimensions of various components of actual working embodiments will be presented. However, it is to be understood that the dimensions, shapes, materials, electrical and electronic capacities, and so forth are examples only, and should not be construed as limiting the scope of the present invention unless specifically stated to be critical.

The base plate assembly 10 has a base plate 11, which in a working example comprises fiberglass reinforced polyester, which has a length of about 21 inches, a width of about 16 inches and a thickness of about 0.5 inch. In preferred embodiments a pair of feet 12 are located near one end of the base plate such that the top surface, which is preferably planar, of the base plate is oriented at an angle of about 4 degrees from horizontal when the apparatus is sitting on a flat surface. It is however, considered to be within the scope of the invention to have additional feet supporting the base plate such that the upper surface of the base plate is oriented substantially horizontally. Furthermore, it is within the scope of the invention to have the base plate incorporated into a structure such as a table top, such that the feet 12 are not required.

As used herein and in the claims relative positions such as "top", "bottom", "upper", "lower", "above", "below" and so forth, are understood to refer to an apparatus which is disposed such that the base plate is disposed horizontally or nearly horizontally, with the other components of the apparatus in the relationships thereto which will be described in the following text.

An arm support 13 is attached to the top surface of the base plate 11 by suitable means for attachment such as adhesives, screws, clips or other fasteners. In a working example the arm support comprises foam rubber and is attached to the top surface of the base plate by a projection on the bottom of the arm rest which is fit into a complementary opening in the base plate. Preferably the arm support comprises a first top surface 14 for supporting a forearm of the person being evaluated, a second top surface 15 for supporting the back side of the palm of the hand, and a third top surface 16 which may support the back side of the fingers during some phases of the assessment procedure. In a working example the forearm supporting surface 14 is disposed at an angle of about 13 degrees from horizontal, the back hand supporting surface 15 is disposed at an angle of about 55 degrees from horizontal, and the included angle $\theta$ between these two surfaces is about 112 degrees. The surface 19 which supports the backs of the fingers is preferably substantially parallel to the top surface of the base plate. This arrangement of the upper surfaces of the arm support is important to the practice of the invention because, as will be shown later, it causes the hand to be hyperextended with respect to the ulnar nerve in a preferred position for application of electrical stimulation to be applied thereto.

A finger grip bar 19 is maintained in position above, and spaced apart from the top surface of the base plate 11 by a pair of supports 20, 21.

The base plate 11 has an elongated slot 22 therein. The elongated slot 22 has a T shaped cross section, when viewed perpendicular to the longitudinal axis of the slot. Preferably the elongated slot 22 and the arm support 13 have longitudinal axes which are parallel to one another. An anchor assembly 24 is assembled with the base plate 11 such that the anchor assembly is capable of movement along the length of the slot as indicated by the arrows in FIG. 1 which are located between the arm support and the elongated slot. In a working example the elongated slot had a width at the top surface of the base plate of about 0.38 inch, a width at the bottom surface of the base plate of about 1.5 inch, and a length of about 8 inches.

The structure of the anchor assembly 24 can be best understood by referring to FIG. 2, which is an exploded view of the assembly, in conjunction with FIG. 1.

A swivel post 25 having a flange 26 disposed at one end thereof and a bore 28 extending completely therethrough is disposed such that the bottom surface of the flange will be adjacent the top surface of the base plate A swivel mount 30 having a bore 31 extending therethrough is slidably mounted on the swivel post, such that the swivel mount 30 may rotate freely and independent of the swivel post. The swivel mount 30 has at least one, and preferably more than one, horizontally oriented threaded holes 32 extending to the exterior surface thereof. Preferably the threaded holes 32 are located at a variety of distances from the ends of the swivel mount, such that the apparatus can be adjusted to accommodate persons of varying sizes.

A T-nut 34 which functions as an anchor post slide is disposed within the elongated slot 22 in the base plate, and has dimensions which are complementary to those of the elongated slot. The T-nut has a vertically oriented threaded hole 35 therein to which a stud 38, threaded at both ends 39, 40, is threadably attached. It is understood, of course, that the T-nut and stud could be machined or molded as a single piece, or could be attached to one another by other means such as an adhesive or welding without deviating from the scope of the present invention.

The stud 38 is disposed vertically and extends through the bore 28 in the swivel post 25. A lock knob 42 having a threaded hole (not shown) in the bottom side thereof is threadably attached to the upper portion 40 of the stud 38. The degree to which the anchor assembly 24 is secured in position with respect to the base plate 11 is controlled by turning the lock knob (as indicated by the arrows near the lock knob in FIG. 1). Thus, the anchor assembly may be loosened by turning the lock knob, moved along the elongated slot 22, and then the lock knob turned to secure the anchor assembly in a desired location. In a working example the overall height of the anchor assembly is about 4⅜ inches, and the threaded holes 32 in the swivel mount 30 are located at heights from the top surface of the base plate ranging from about 1¼ inch to about 2¼ inch.

A transducer 43 having a threaded stud 44 extending therefrom is threadably attached to the swivel mount 30 via one of the threaded holes 32. A signal lead 45 and a cable 46 extend from the transducer. A leather or plastic ring 47 is attached to an end of the cable 46 which is distal from the transducer 43. A working embodiment employees a 25 or 100 pound load cell transducer, manufactured by Sensotec, Inc. of Columbus, Ohio U.S.A. and sold under the trade designation(s) AL311BL-25 lb and/or AL311BR-100 lb.

Figure 3:
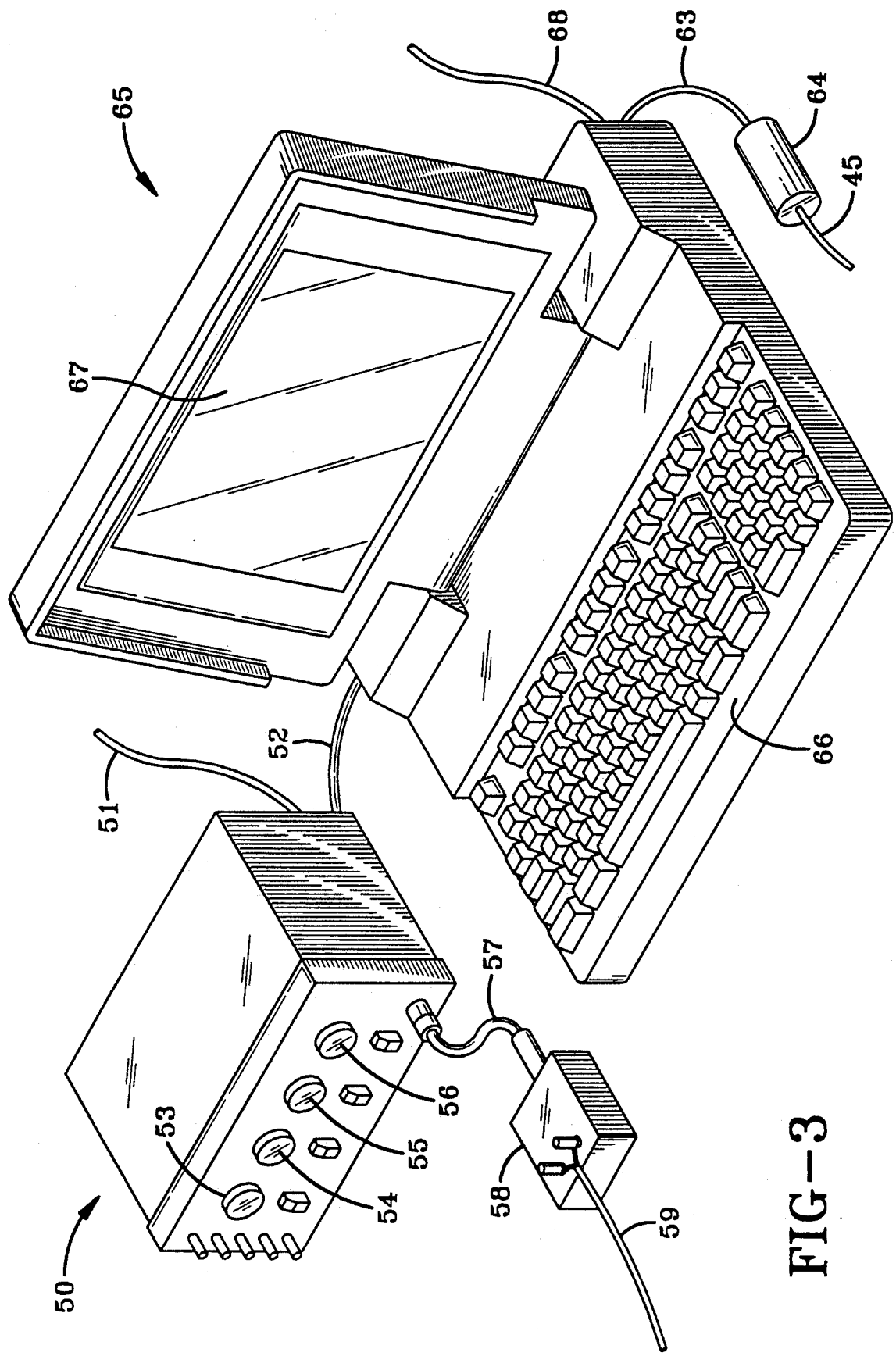
FIG. 3 is a pictorial representation of a computer and a source of electrical potential which are components of a muscle function assessment device.

Referring next to FIG. 3 there is shown a pictorial representation of a stimulus generator 50 and a computer 65 which are components of a muscle force assessment apparatus. The stimulus generator 50 is connected to a source of electricity such as a common 110 volt wall outlet, by a power cord 51. A plurality of controls 53, 54, 55, 56 are employed for controlling such parameters as stimulus frequency, pulse duration, delay, and voltage. A working example employed a commercially available stimulus generator manufactured by Grass Instruments of Quincy, Mass., U.S.A. and sold under the trade name S44 Stimulus Generator. An isolation interface cable 57 connects the stimulus generator with an isolation interface 58 which functions to electrically isolate the subject from AC power and provide a constant current source. A working example employed a commercially available isolation interface manufactured by Grass Instruments of Quincy, Mass., U.S.A. and sold under the trade name SU17 isolation interface which has the capacity of 0 to 15 milliamps of output drive current.

An electrode lead 59 extends from the isolation interface 58 to electrodes (not shown) which are employed in the muscle force assessment procedure.

A computer 65 is connected to the stimulus generator 50 via a stimulus interface cable 52, and to a source of electricity, such as a 110 volt wall outlet, by a power cord 68. The computer has a keyboard 66 and viewing screen 67, as well as a central processing unit and memory unit. A transducer amplifier cable 63 extends from the computer to a transducer amplifier 64 which functions to amplify a signal from the transducer and provide incitation voltage to the transducer. A working example employs an amplifier manufactured by Sensotec, Inc. of Columbus, Ohio U.S.A. and distributed under the trade designation Model BE113#VPV. A signal lead 45 extends from the transducer amplifier to the transducer which has been described in regards to FIGS. 1 and 2. A working embodiment employs a Toshiba 3200-SX computer, having a Metrabyte DAS-8PGA analog to digital converter which was installed as an auxiliary board therein. However, any IBM compatible computer could be employed with the invention. It is understood that in a preferred embodiment the stimulus generator and computer may be integrated into a single unit such that the parameters controlled by the stimulus generator can be input via the computer keyboard.

Figure 4:
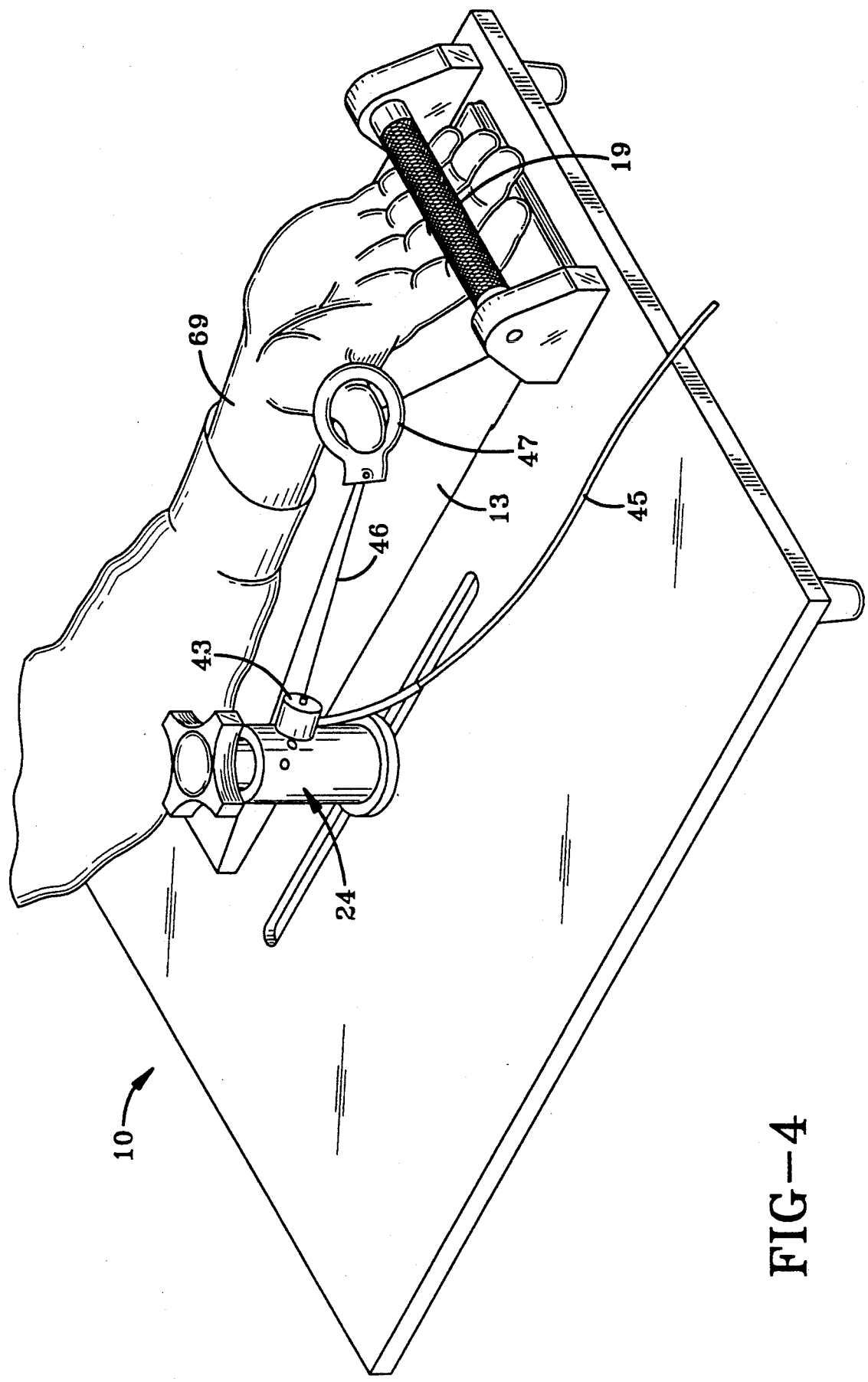
FIG. 4 is a pictorial representation of the base plate assembly of FIG. 1 with the forearm and hand of a person in position for a muscle force assessment procedure.

Referring next to FIG. 4 there is shown the base plate assembly IO of FIG. 1 with the forearm and hand 69 of a person (the subject) resting upon the arm support 13 and the fingers adjacent the finger grip bar 19. The leather or plastic ring 47 has been placed around the thumb such that the ring is against the palm of the hand. A cable 46 connects the ring 47 to the transducer 43, which in turn has been threadably attached to the anchor assembly 24. The location of the anchor assembly has been adjusted such that the tension on the thumb is such that a maximum force is observed when a stimulus is applied to the subject's wrist as determined using the apparatus in a manner that will be described later.

Figure 5:
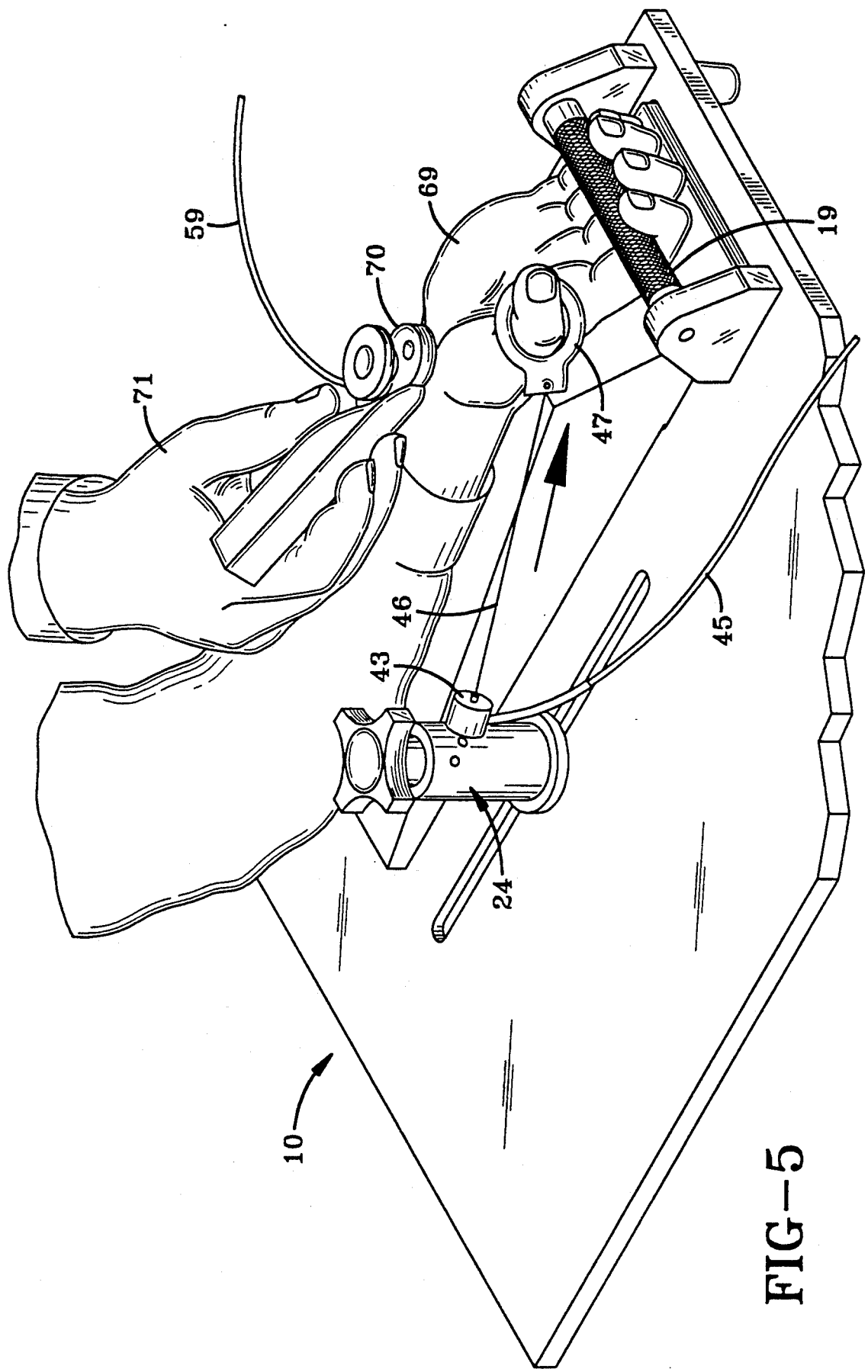
FIG. 5 is a pictorial representation of the muscle force assessment procedure.

The subject is now ready to be subjected to electrical stimulation as illustrated in FIG. 5. A qualified trained technician or health care professional 71 places electrodes 70 on the subject's arm, 69. The electrodes are connected to the isolation interface (FIG. 3) via the electrode lead 59. An electrical potential is applied across the electrodes and the ulnar nerve is stimulated, contracting the adductor pollicis and causing the fingers to grip the finger grip bar 19. The thumb exerts tension on the cable 46 which extends from the leather or plastic ring 47 to the transducer 43 which is threadably attached to the anchor assembly 24. The transducer generates an electrical signal which is transmitted via the signal lead 45 to a transducer signal amplifier and computer (not shown). A preferred method of assessing the muscle force will be described with reference to FIGS. 6-12 which are pictorial representations of what may appear on the computer screen during various phases of the assessment procedure.

The computer program contains parameters which may be changed as required such as load cell capacity, data file path, printer type, number of data points in a moving average filter, and A to D converter base address. These parameters vary based upon the computer and various components of the apparatus which may be selected by the engineer or operator. The program contains means for adjusting these parameters, which are changed only infrequently, but not normally for each subject being evaluated.

Referring next to FIG. 6 there is shown an example of what may appear on the computer screen when a qualified trained technician or health care professional (hereinafter referred to as the "operator"), is preparing to perform a muscle function assessment on a subject. It is understood that all of the computer screen formats which are presented herein are examples only, and that the formats may be altered without deviating from the scope of the present invention. In a working example the screen format of FIG. 6 is the first one that appears when conducting a muscle function assessment. The operator selects the file for the subject who is being tested, or creates a new file if the subject has not been previously evaluated. On the lower portion of the screen, below the double horizontal lines, is shown the file which has been selected, in this instance for SUBJECT 1. The operator now pushes the RETURN/ENTER key to advance to the next screen.

The format presented in FIG. 7 now appears on the computer screen. Information regarding the subject can be stored in the subject's file so that when the subject is evaluated in the future the same parameters can be used, or selected parameters can be changed. In the working example a set of parameters may also be stored in a file such that if another subject, for example SUBJECT 8, is to be evaluated using the same parameters as SUBJECT 1, the set of parameters can be easily transferred to SUBJECT 8's file. By pressing the S key on the keyboard the operator selects the capacity to input various information about the subject including: name, weight, height, age, the date of the test the file name, and any comments about the subject that the operator may find to be useful. Located near the center of the screen is an area for recording the strength of the subject's grip, if desired. This grip data relates to the subject's voluntary gripping of a device, such as a hand dynamometer, not in reaction to an external electrical stimulus. At the right side of this screen, are presented test parameters which may be altered as required, with the capacity to store more than one set of test parameters for a subject. These parameters are elaborated upon below.

"Lead In" —refers to the time interval between the beginning of a test cycle and the application of an electrical stimulus to the subject. For example with reference to FIG. 7, while holding the electrodes against the subject's wrists, the operator pushes the RETURN key to begin the test cycle, and 1.1 seconds later the electrical stimulus begins.

"S-Duration" relates to the length of time that the stimulus is applied to the subject, for example, with reference to FIG. 7, 1.0 second.

Lead Out relates to the length of the processing time from the cessation of the stimulus until the recording of data ends. In the working example each test cycle is programmed to be 6 seconds long, and Lead-Out time is 6 seconds minus the Lead-In and S-Duration. For example, a 6 second test cycle may comprise a 1 second lead in, 1 second of stimulation, and four seconds of lead out.

"S-Intensity" relates to the stimulus current in milliamps.

"S-Frequency" relates to the stimulus frequency in cycles per second. Preferably the subject will be stimulated with a variety of frequencies, for example 10, 30 and 50 cycles per second during the assessment procedure. Of course, any desired and appropriate frequencies may be used.

"S-Width" relates to pulse duration of the stimulus in microseconds.

"Force Peak" and "Relax Rate" (more properly Relaxation Rate) are test results. In FIG. 7 test results for earlier tests are presented by way of example. "Force Peak" is presented both in Newtons for each test cycle and as a percentage of the peak force for any selected set of parameters chosen from those displayed on the screen, compared to one another. The set of parameters chosen as a base are indicated by a diamond shaped cursor in the "Parameters" line of the screen. It is anticipated that the operator will usually choose the test results (plotted as a curve to be described later) with the highest stimulus frequency as the base, thus showing a relationship between peak force and the frequency of the stimulus.

Figure 8:
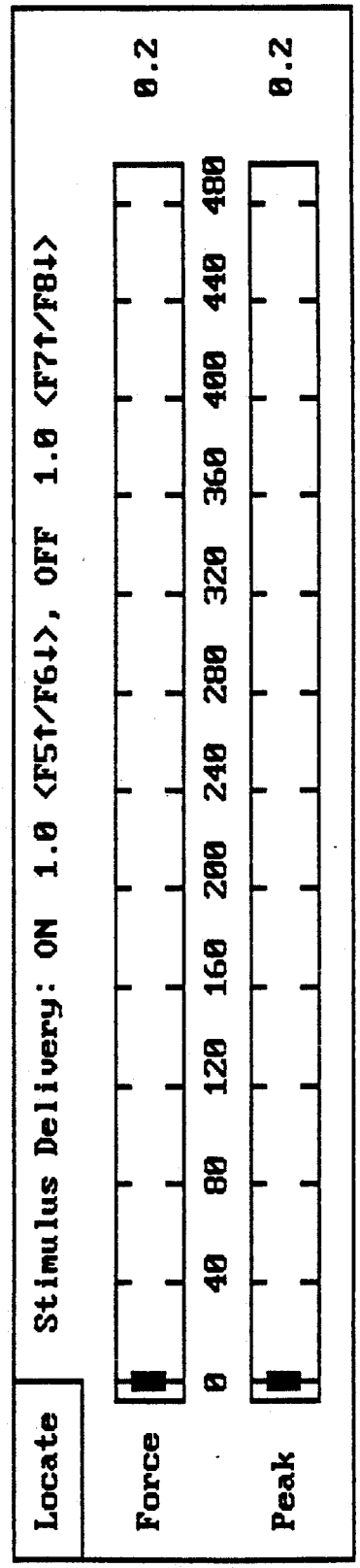
Figure 9:
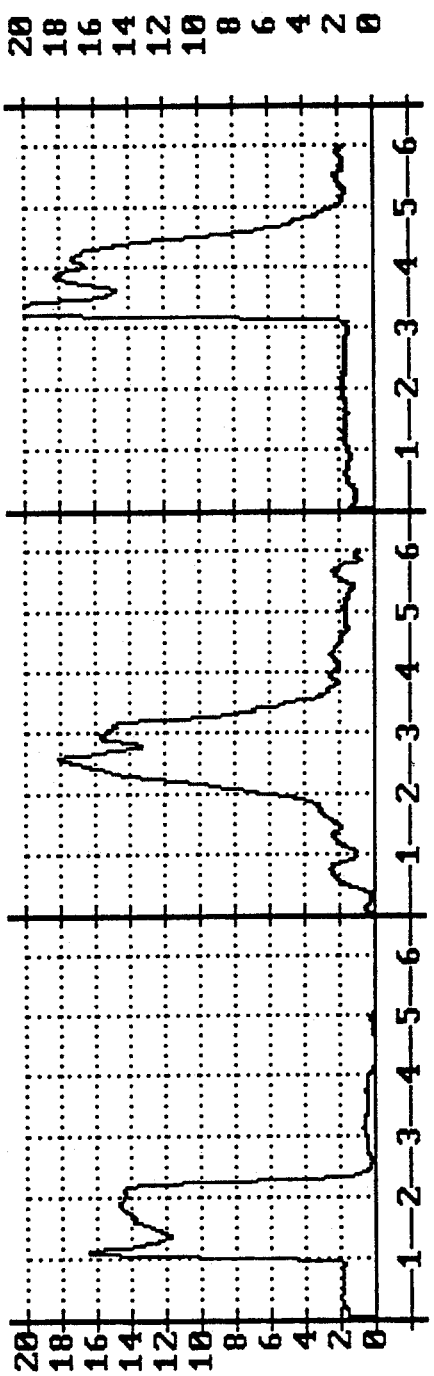

At this point the operator may elect to go to either the screen shown in FIG. 8 or the screen shown in FIG. 9, but most typically will select FIG. 9. The operator depresses the space bar on the computer keyboard to advance to the screen shown in FIG. 9.

FIG. 9 is a computer screen that is similar to FIG. 7, but includes in the lower portion of the screen graphic representations of results from prior tests run on the subject. The three side-by-side graphs represent tests run with parameter sets 1/1, 2/1, and 3/1 respectively. In a working example, for each of the parameter sets a number of graphs may be stored. By analogy, for each set of test parameters that have been used for earlier tests there is a Rolodex ® of graphs which may be viewed sequentially using the "Page Up" key on the computer keyboard. The diamond shaped cursor in the box at the upper right hand portion of the screen is used to select the set of parameters for which the results may be scrolled through.

The operator may elect to bring up the format shown in FIG. 8 from either the screen shown in FIG. 7 or the screen shown in FIG. 9. The FIG. 8 screen relates to the use of the computer to properly locate the electrodes on the subject's wrist with respect to the ulnar nerve. In the lower portion of this screen is a continuous read out of the force exerted by the subject's adductor pollicis muscle in response to an electrical stimulus supplied by the electrodes. A horizontal column labeled "Force" presents the current force exerted by the adductor pollicis as detected by the load cell which is a part of the base plate assembly described above. The horizontal column labeled "Peak" records the maximum force exerted by the adductor pollicis during a stimulation cycle. Electrode location tests are repeated until the electrode location giving the largest deflection on the "Peak" column is determined, and that electrode location is then used for making the muscle function assessment. At this time the location of the anchor assembly 24 (FIG. 5) in the longitudinal slot is adjusted so that the tension placed on the subject's thumb via the cable 46 will result in a peak force being indicated in PEAK column on the computer screen when a stimulus is applied by the operator. The operator now presses the ESCAPE key to return to the screen format shown in FIG. 9.

At this time, with the screen format shown in FIG. 9 appearing on the computer screen, the operator depresses the space bar on the computer's keyboard to begin a test cycle using the set of parameters indicated by the diamond shape cursor in the upper right hand portion of the screen. The screen format shown in FIG. 12 will automatically appear on the computer screen. In the lower portion of the screen is a graph which has two items plotted thereon. Towards the top of the graph is a plot, in straight lines, of the stimulus signal delivered to the subject. A plot of the force exerted by the subject's adductor pollicis in response to the stimulus is also shown. The horizontal axis of this graph is calibrated in seconds, and the vertical axis is calibrated in newtons. The scale of the vertical axis is adjustable in order to accommodate various subjects and to allow the operator to view the results at various levels of magnification. The operator may initiate another test cycle by once again depressing the space bar of the computers keyboard, or may press the escape key on the computer keyboard to return to the screen format shown in FIG. 9.

Figure 10:
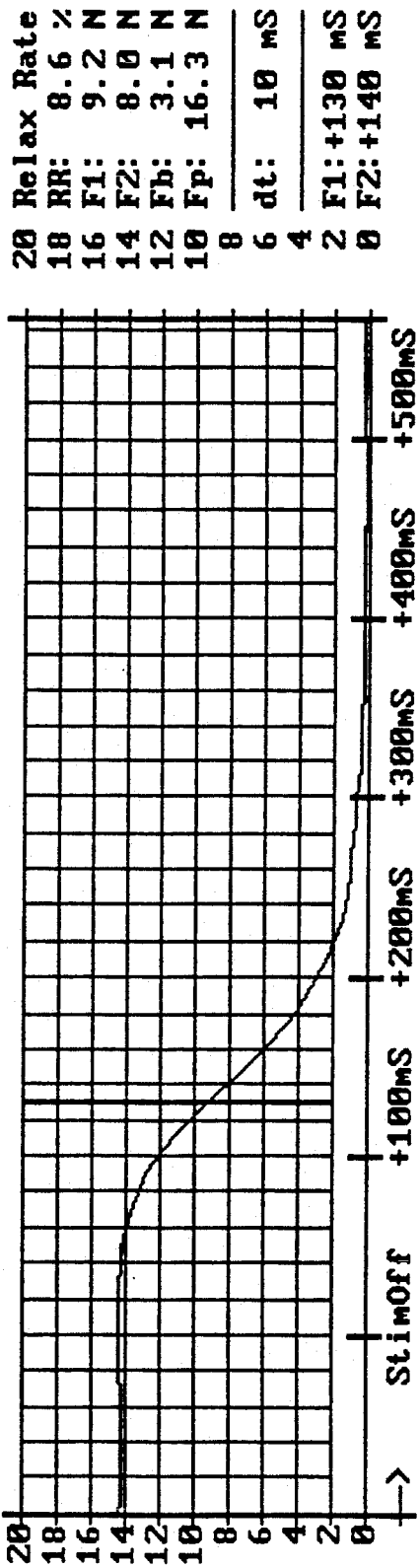

At this time the operator may select to depress the "R" key of the computer's keyboard to display the screen format shown in FIG. 10, which presents an enlarged view of the decaying portion of the force curve generated during the test cycle. In this screen format the portion of the force curve which is shown extends from a time 100 milliseconds prior to termination of the stimulus to nearly 600 milliseconds after termination of the stimulus.

Computations for relaxation rate are made and displayed along with the numbers used in the computations. The data is as follows: RR (Relaxation Rate), F1(One of two consecutive data points with the greatest slope), F2 (The second of two consecutive data points with the greatest slope), Fb (Average force recorded from starting a test cycle to application of the electrical stimulus), Fp (Peak force during stimulus). The calculation for RR is as follows:

$$\text{Relaxation Rate} = \frac{F_1 - F_2}{F_p - F_b} * 100$$

Also displayed is the time between the two points F1 and F2 (dt), and the location in time (ms) of F1 and F2 from the termination of stimulus.

Two lines bisect the data curve at the two points in which the software located the two points having the greatest slope after termination of the stimulus (F1 and F2). The operator may change the two F1 and F2 points by using the arrow keys and locating the two bisecting lines at new positions on the data curve. The calculation of Relaxation Rate is updated as the two new F1 and F2 points are chosen.

In FIG. 10 the $F_1$ and $F_2$ points are very near one another due to the steep slope of the curve, such that the vertical lines intersecting $F_1$ and $F_2$ appear as a single heavy line located at about 115 mS on the horizontal axis of the graph.

Figure 11:
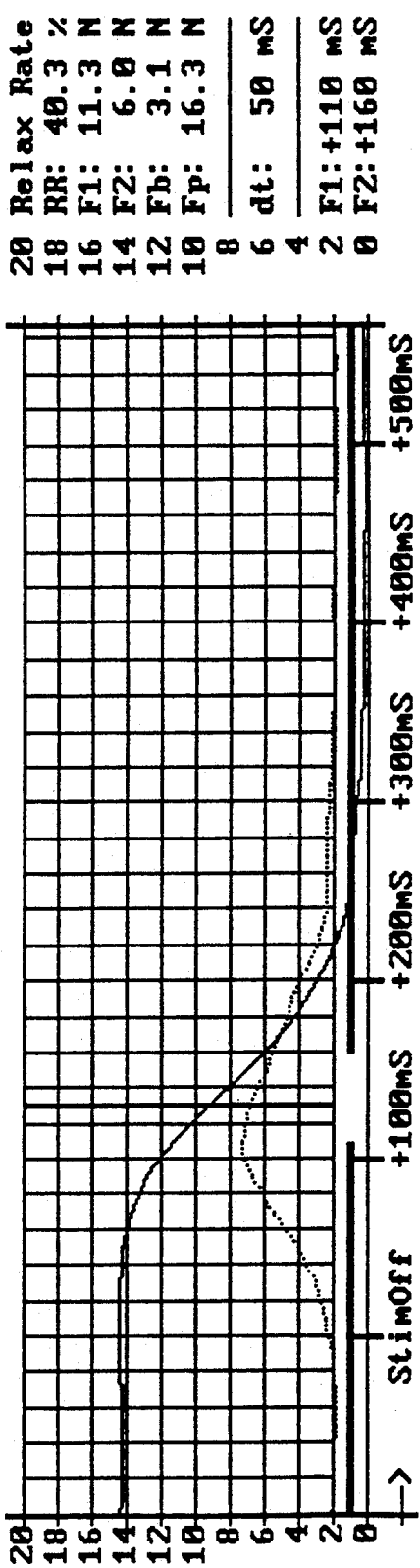
Figure 12:
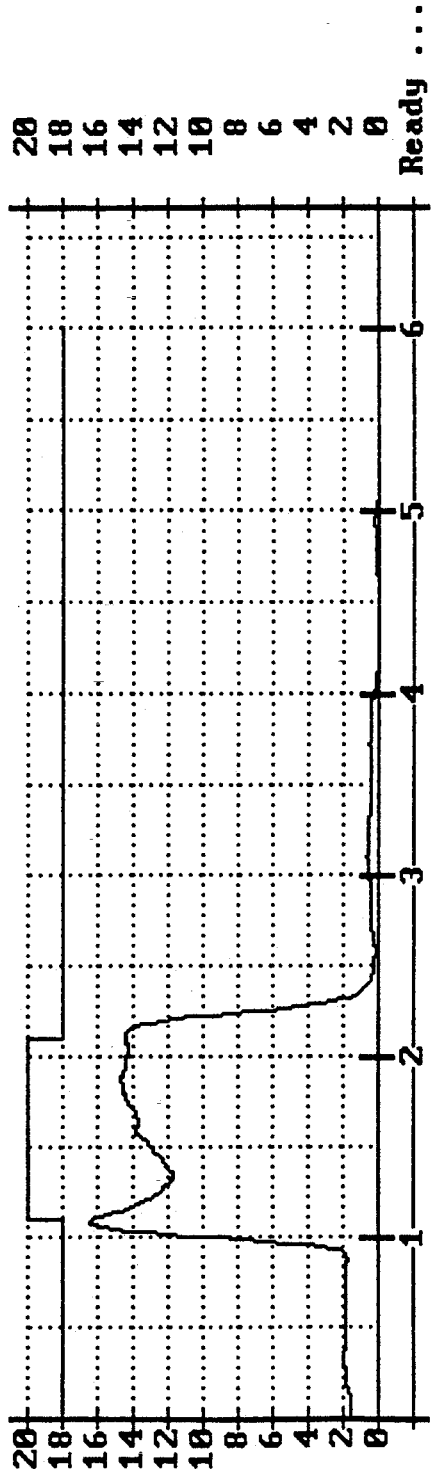

At this time the operator may elect to depress either the up/down or left/right arrow keys of the computer's keyboard to cause the screen format shown in FIG. 11 to appear on the computer's screen. This screen format is similar to that shown in FIG. 11, but it shows two curves plotted on the graph. The curve which intersects the vertical axis at about 14 newtons is the one shown in FIG. 11, while the other curve is the first derivative of that curve based upon the time between $F_1$ and $F_2$ (10 milliseconds). The operator may chose to change $F_1$ and/or $F_2$, and in that event the plotted derivative will be altered accordingly.

The % Peak Force which is displayed on the various screen formats is calculated by the computer as follows:

$$\frac{\%}{\text{PEAK FORCE}} = \frac{\text{FORCEpeak}_1 - \text{FORCEbaseline}_1}{\text{FORCEpeak}_2 - \text{FORCEbaseline}_2} \cdot 100\%$$

WHERE: FORCEpeak$_2$ is peak force of the data curve being referenced as 100%

FORCEbaseline$_n$ is the average force applied to the force transducer from the time in which the experiment is executed to the start of stimulus.

FORCEpeak$_1$ = is the peak force of the data curve that is being referenced to the FORCEpeak$_2$.

Figure 13:
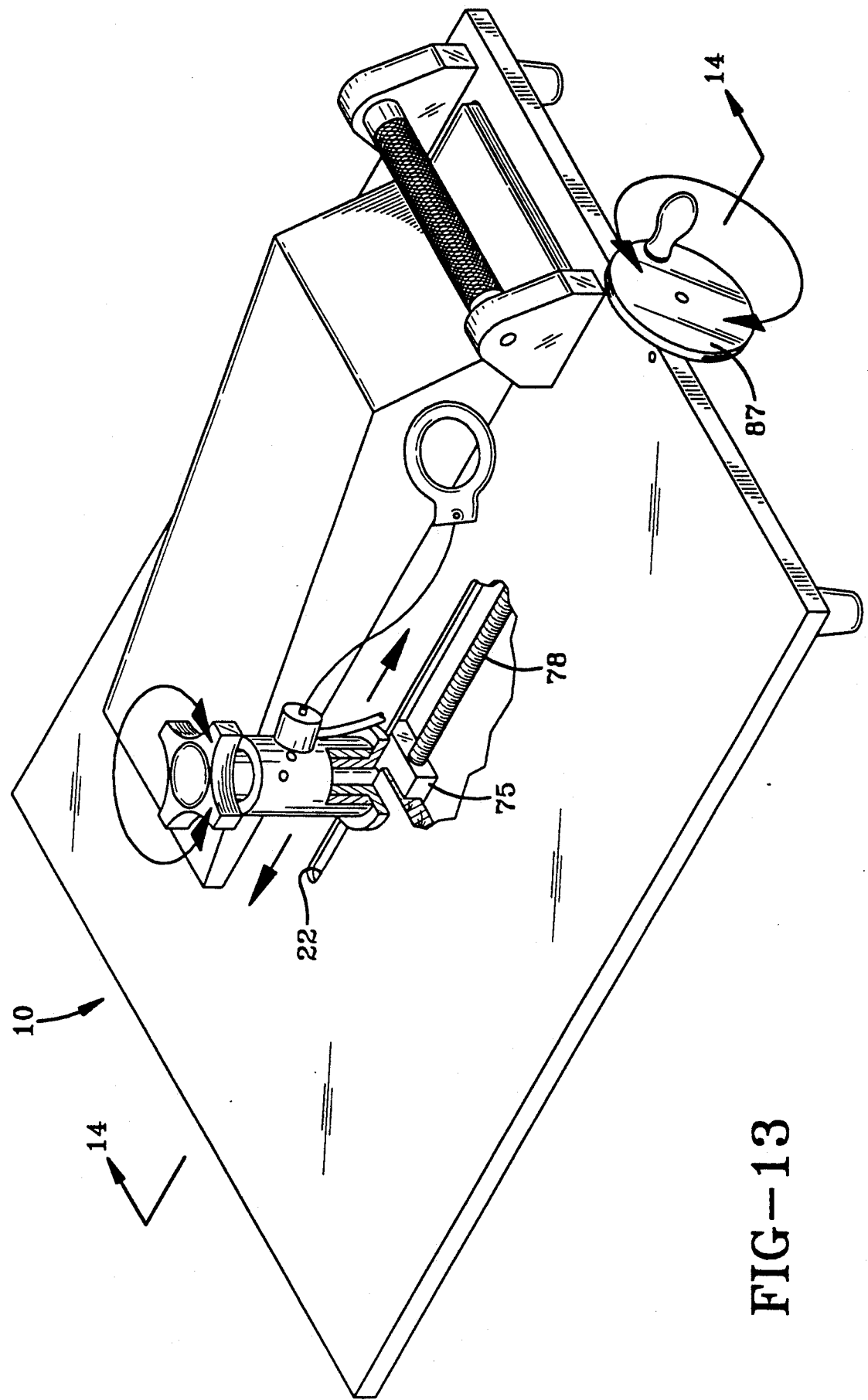
FIG. 13 is a perspective view, partially broken away of a base plate assembly according to a preferred embodiment having a lead screw assembly for adjusting tension on the thumb of a person being assessed.
Figure 14:
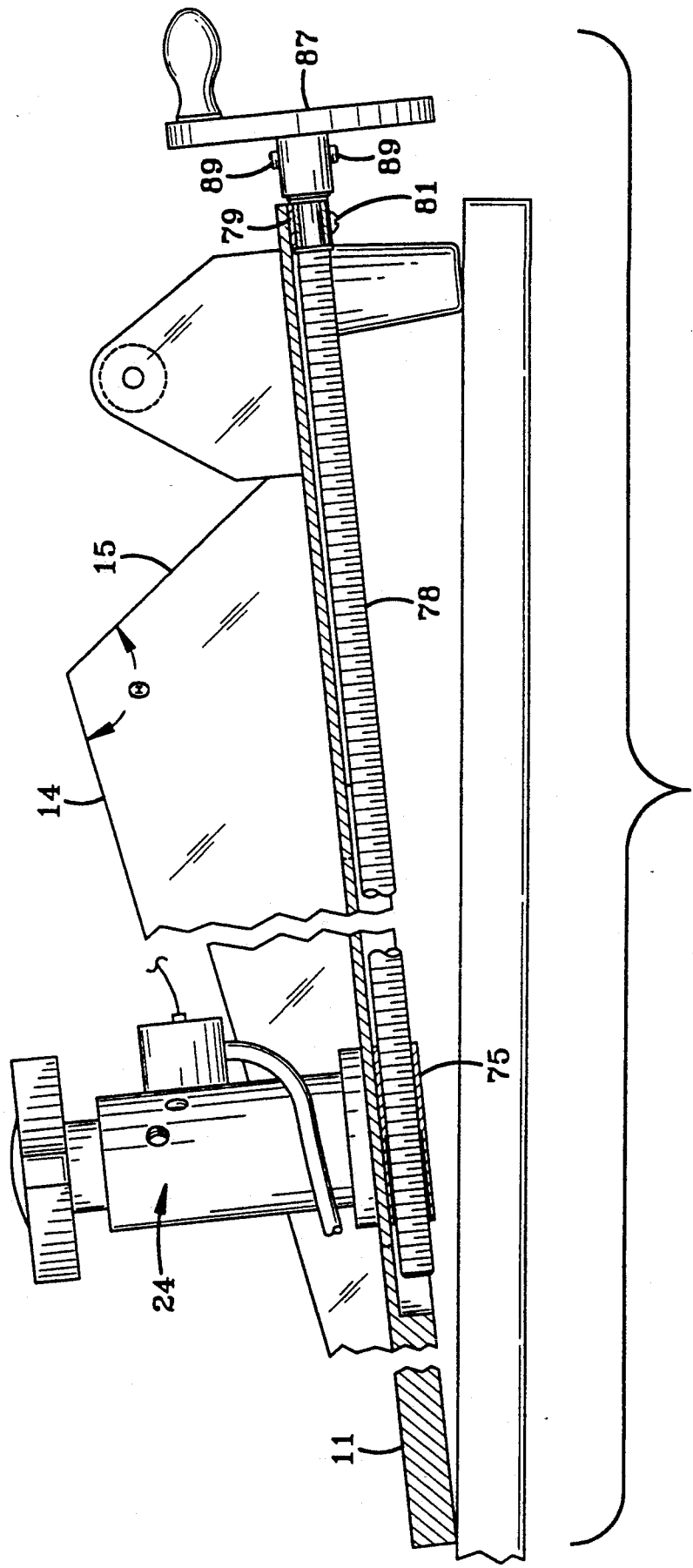
FIG. 14 is a sectional view of the base plate assembly of Fig. looking in the direction of arrows 14—14 in FIG. 13.
Figure 15:
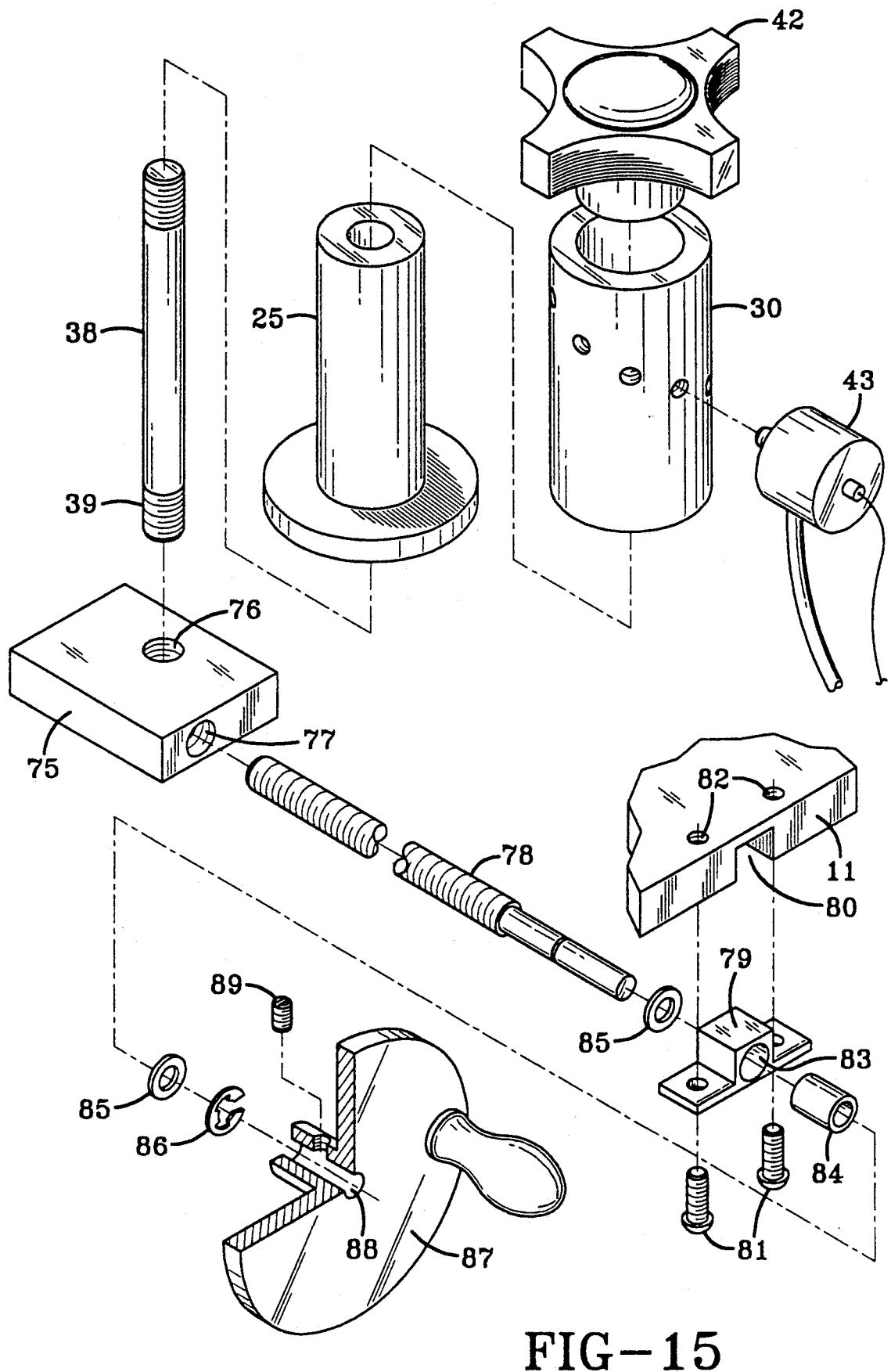
FIG. 15 is an exploded view of an anchor/lead screw assembly which is a component of the base plate assembly of FIG. 13.

Referring next to FIGS. 13-15 there is shown a base plate assembly 10 according to a more preferred embodiment of the invention. In this more preferred embodiment a lead screw mechanism is provided for making fine adjustments to the position of the anchor assembly 24. The swivel post 25, swivel mount 30, stud 38, lock knob 42, and transducer 43 of the anchor assembly 24 are substantially the same as those shown in FIG. 2 and described in the specification.

The anchor post slide 75 is located in the elongated groove 22 in the base plate 11. The groove 22 has a T-shaped cross section as has been already described. The anchor post slide has a threaded vertical hole 75 therein for threadably engaging a threaded portion 39 of the stud 38. The anchor assembly 24 is assembled in substantially the same manner described above with respect to FIG. 2, with the anchor post slide substituted for the T-nut. A horizontal bore 77 extends through the anchor post slide, and is threaded along at least a portion of its length. A portion of the length of a lead screw 78 is disposed within the horizontal bore 77 in the anchor post slide, such that the lead screw threadably engages the anchor post slide.

A lead screw hanger 79, having a T shaped cross section, is at least partially disposed within a notch 80 located on the underside of the base plate 11. A pair of screws 81 extend through apertures in the lead screw hanger to threadably engage the base plate via threaded holes 82 therein. Of course, the lead screw hanger may be secured to the base plate by any suitable means for attachment such as an adhesive, welding, nuts and bolts, and so forth. The lead screw hanger 79 has a horizontal bore 83 therethrough which preferably has a press-fit bushing 84 secured therein by means of an interference fit.

The lead screw 78 passes through a thrust washer 85, the bushing 84, another thrust washer 85, and then has a retainer clip 86 snapped onto the lead screw to limit the horizontal movement of the lead screw. A crank handle 87, having a bore 88 therein is slid over the lead screw and is secured in place by at least one set screw 89.

As best shown in FIG. 13 the crank handle 87 is rotated, which causes the lead screw 78 to advance the anchor assembly along the groove 22. The lock knob is turned in order to either secure the anchor assembly in a desired location or release the anchor assembly so that it can be moved.

Figure 16:
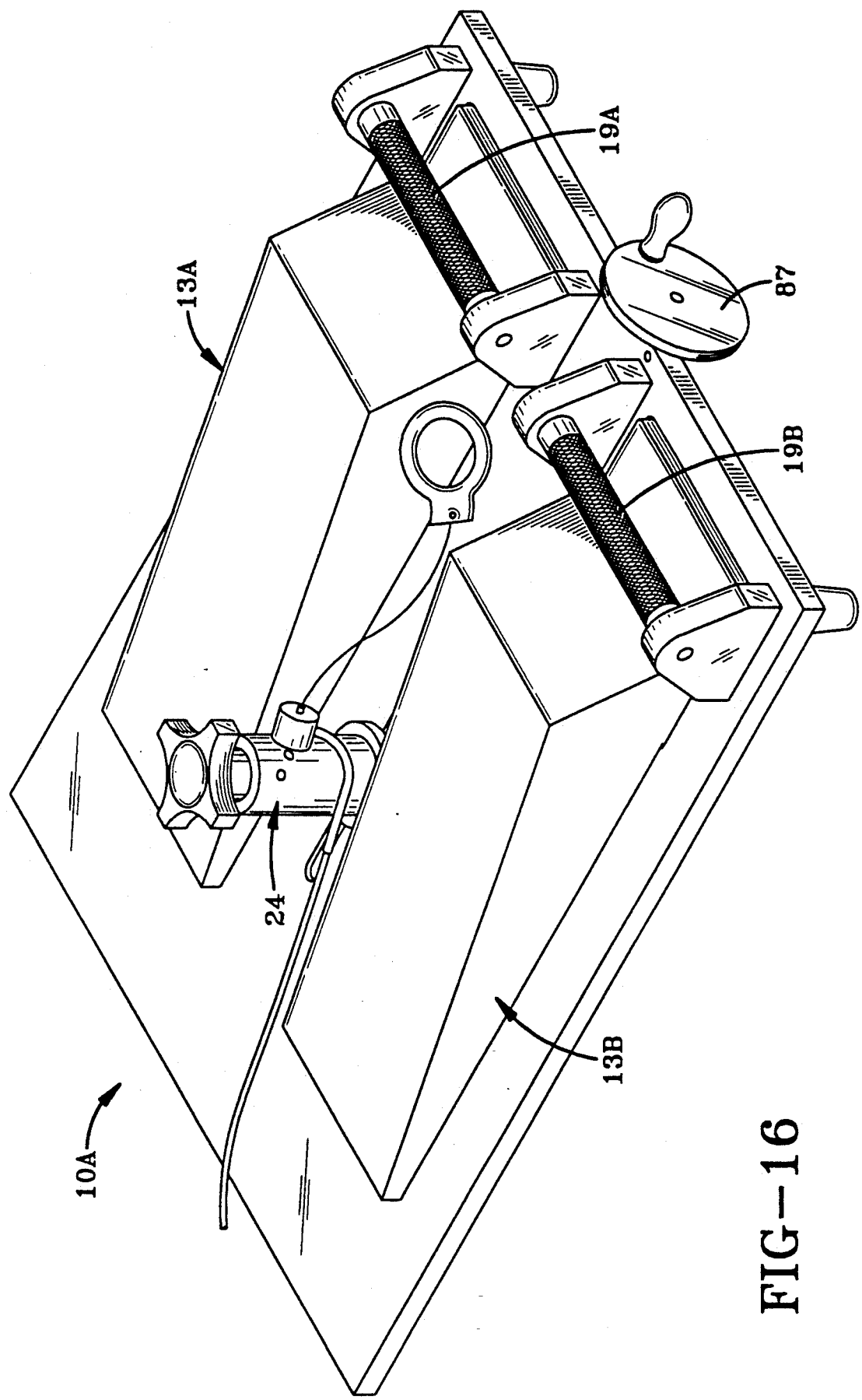
FIG. 16 is a perspective view of a base plate assembly according to a most preferred embodiment.

A most preferred embodiment of a base plate assembly 10A of an apparatus for performing muscle function assessment is shown in FIG. 16. This most preferred embodiment comprises two arm supports 13A, 13B, and two finger grip bars 19A, 19B, substantially identical to those which have been described herein in detail. The arm supports are oriented substantially parallel to one another, with the crank handle 87 for a lead screw mechanism, and an anchor assembly 24 interposed between the arm supports. This most preferred embodiment allows either hand of a person to be utilized when performing a muscle force analysis.

While certain representative embodiments and details have been shown for the purpose of illustrating the invention, it will be apparent to those skilled in the art that various changes and modifications may be made therein without departing from the spirit or scope of the invention.

We claim:
1. An apparatus for assessing muscle force of the adductor pollicis muscle comprising:
   (a) a base plate assembly comprising (i) a base plate, (ii) means attached to the baseplate for supporting the forearm, wrist and hand of a person, such that the palm of the hand is up and the wrist is flexed such that the included angle between the forearm and back of the hand is an obtuse angle, (iii) a finger grip bar attached to the base plate adjacent said means for supporting, (iv) an anchor post slideably located within a groove in the base plate, said groove extending parallel to the means for supporting a person's forearm, wrist, and hand, said anchor post having a load cell attached thereto with a cable extending from the load cell to a thumb holding means for receiving and holding the thumb of a person;
   (b) electrodes for providing an electrical stimulus to the ulnar nerve of a person;
   (c) a computer which is in communication with the load cell via a conductive cable, said computer being capable of receiving, storing and plotting a graph of signals from the load cell regarding forces exerted on the load cell by the thumb of a person, whose ulnar nerve has been subjected to electrical stimulation by said electrodes, via the thumb holding means and the cable extending therefrom to the load cell, said computer being programmed to aid in locating the electrodes with respect to a person's ulnar nerve by determining and optimizing tension placed on a person's thumb by the thumb holding means and cable extending therefrom to the load cell which is attached to the slidable anchor post, said computer being programmed to determine the relaxation rate of a person's adductor pollicis muscle using the equation

$$\text{Relaxation Rate} = \frac{F_1 - F_2}{F_p - F_b} \cdot 100$$

wherein $F_1$ and $F_2$ are two consecutive data points having the greatest slope between them on a graph of the forces in Newtons exerted on the load cell as presented on the graph located after the cessation of the stimulus, $F_p$ is the peak force in Newtons exerted by the thumb during the electrical stimulation and $F_b$ is the average force in Newtons exerted by the thumb from the beginning of a test cycle until the application of the electrical stimulus.

2. An apparatus according to claim 1 further comprising a lead screw for adjusting the location of the anchor post.

3. An apparatus according to claim 2 further comprising a second means for supporting the forearm and wrist of a person substantially identical to the first such means for supporting, said second means being attached to said base plate such that the elongated slot in the base plate is disposed between said two means for supporting and extends parallel to both of said means for supporting, said second means for supporting having a finger grip bar associated therewith, such that either arm of a person may be used in a muscle function assessment procedure.

4. An apparatus according to claim 1 further comprising a second means for supporting the forearm and wrist of a person substantially identical to the first such means for supporting, said second means being attached to said base plate such that the elongated slot in the base plate is disposed between said two means for supporting and extends parallel to both of said means for supporting, said second means for supporting having a finger grip bar associated therewith.

5. An apparatus according to claim 1 wherein computer is programmed to display in a graphic format at one time the resulting force data from more than one muscle force assessment procedure.

6. An apparatus according to claim 5 wherein the computer is programmed to store information regarding a person whose muscle function is assessed using the apparatus.

7. An apparatus according to claim 1 wherein the computer is programmed to store information regarding a person whose muscle function is assessed using the apparatus.

* * * * *

UNITED STATES PATENT AND TRADEMARK OFFICE
CERTIFICATE OF CORRECTION

PATENT NO. : 5,263,490

DATED : November 23, 1993

INVENTOR(S) : J. Hayes, J. Tiefenthal, M. McCamish, J. Ross

It is certified that error appears in the above-identified patent and that said Letters Patent is hereby corrected as shown below:

Column 5, line 30, "IO" should be --10--.

Signed and Sealed this

Seventeenth Day of May, 1994

Attest:

BRUCE LEHMAN

*Attesting Officer*    *Commissioner of Patents and Trademarks*